United States Patent
Castán Barberán et al.

(10) Patent No.: US 6,949,492 B2
(45) Date of Patent: Sep. 27, 2005

(54) AQUEOUS NACREOUS CONCENTRATE COMPOSITIONS COMPRISING ETHOXYLATED GLYCERIDES

(75) Inventors: Pilar Castán Barberán, Barcelona (ES); Hiroshi Abe, Barcelona (ES)

(73) Assignee: Kao Corporation, Tokyo (JP)

(*) Notice: Subject to any disclaimer, the term of this patent is extended or adjusted under 35 U.S.C. 154(b) by 62 days.

(21) Appl. No.: 10/484,813

(22) PCT Filed: Feb. 14, 2002

(86) PCT No.: PCT/EP02/01570

§ 371 (c)(1),
(2), (4) Date: Jan. 30, 2004

(87) PCT Pub. No.: WO03/011246

PCT Pub. Date: Feb. 13, 2003

(65) Prior Publication Data

US 2004/0214740 A1 Oct. 28, 2004

(30) Foreign Application Priority Data

Jul. 30, 2001 (ES) .......................... 200101780

(51) Int. Cl.[7] .............. C11D 1/83; C11D 3/37; A61K 7/06; A61K 7/48; A61K 7/50
(52) U.S. Cl. ............ 510/127; 510/405; 510/424; 510/426; 510/475; 510/492; 510/505; 424/401; 424/70.5; 424/70.11; 424/70.24

(58) Field of Search ................. 510/127, 405, 510/424, 426, 475, 492, 505; 424/401, 70.5, 70.11, 70.24

(56) References Cited

U.S. PATENT DOCUMENTS

| | | | |
|---|---|---|---|
| 5,466,395 A | 11/1995 | Tosaka et al. | |
| 6,210,659 B1 * | 4/2001 | Wilhelm et al. | 424/70.24 |
| 2004/0214740 A1 * | 10/2004 | Barberan et al. | 510/421 |

FOREIGN PATENT DOCUMENTS

| | | |
|---|---|---|
| DE | 199 37 298 | 2/2001 |
| EP | 0 268 992 | 6/1988 |
| EP | 0 300 379 | 1/1989 |
| EP | 0 684 302 | 11/1995 |
| JP | 55-38333 | 3/1980 |
| WO | 98 20844 | 5/1998 |

* cited by examiner

*Primary Examiner*—Brian P. Mruk
(74) *Attorney, Agent, or Firm*—Oblon, Spivak, McClelland, Maier & Neustadt, P.C.

(57) ABSTRACT

New aqueous nacreous concentrated compositions, containing ethoxylated glycerides derived from carboxylic acids having 6 to 22 carbon atoms as emulsifying and/or dispersing agent are provided which show all the essential features required for this kind of composition, such as storage stability, excellent nacreous appearance, besides the possibility of acting as thickening agents and increasing the foaming power of the personal care cosmetic products.

13 Claims, No Drawings

AQUEOUS NACREOUS CONCENTRATE COMPOSITIONS COMPRISING ETHOXYLATED GLYCERIDES

TECHNICAL FIELD

The present invention relates to novel aqueous nacreous concentrate compositions, containing ethoxylated glycerides derived from carboxylic acids having 6 to 22 carbon atoms as emulsifying and/or dispersing agents.

PRIOR ART

For years, the nacreous or iridescent appearance has been used in personal care products (cosmetic products for the personal and hair hygiene) as well as in household cleaning products (dishwashing detergents, laundry detergents, etc.).

This nacreous appearance improves the final presentation of the aforementioned products, making them more attractive to the consumers.

As it is well known, in order to obtain a nacreous appearance different materials can be used, e.g. inorganic substances in powder form (mica, lead, mercury, bismuth oxychloride, titanium dioxide, etc.). Nevertheless, these substances are too harmful to be included in formulations for personal hygiene or for household cleaning. Organic substances such as metallic salts of fatty acids, fatty acids glycol esters and fatty acid alkanolamides can also be used.

To obtain nacreous personal hygiene formulations, fluid aqueous nacreous concentrates, containing the organic substances that exhibit the nacreous or iridescent appearance, are added, without heating, to aqueous surfactant solutions.

It is well known that the concentrates that exhibit the nacreous or iridescent appearance are prepared from:
- one or more components that exhibit the nacreous appearance, like fatty acid ethylene glycol esters or fatty acid propylene glycol esters, like palmitic acid, stearic acid or behenic acid ethylene or propylene glycol esters; fatty monoalkanolamides; saturated linear fatty acids, etc.
- emulsifier or dispersing agents, that could be one or more surfactants
- crystallisation adjuvant agents, like polyols, optionally ethoxylated, fatty acid ethanolamides optionally ethoxylated, glycerol polyesters, etc.
- other components, like preservatives, pH buffering agents, thickening agents, etc.

Traditionally, alkanolamides were used in nacreous compositions to increase the iridescent appearance. However, these compounds are involved in the formation of harmful substances like N-nitrosamines.

More recently, glycol esters have been introduced in personal care formulations. As already mentioned, the preferred way to incorporate a nacreous agent, like glycol esters, in personal care formulations, is preparing aqueous nacreous concentrates, which are later added, without heating, to the final formulations.

It is well known to the skilled in the art that glycol esters are difficult to dissolve and/or disperse in surfactant solutions. The required concentration to obtain the desired nacreous appearance will depend on the effectiveness of the crystalline dispersion.

On the other hand, it is convenient for a nacreous concentrate not to have a too complex composition in order to be obtained easily and at low cost, although having a high organic content, to avoid the use of preservatives.

The patent application JP-55038333, describes the use of ethoxylated fatty acid monoesters as emulsifiers in a cosmetic cream composition, to avoid the precipitation of nacreous crystals during storage.

The patent application EP-A-268992 describes concentrate nacreous compositions which can contain 5–15% ethylene glycol distearate, 1–6% fatty acid monoethanolamide, and 2–8% of an emulsifier that can be, among others, a fatty acid monoester or diester of an ethoxylated glycerol.

In the patent application EP-A-300379 are described concentrate nacreous compositions free from alkanolamides, that can contain 5–20% saturated linear acid, 0–6% ethylene glycol distearate, and 3–10% of an emulsifier that, as it is mentioned in the examples, corresponds to a mixture of ethoxylated fatty alcohols, monoester of an ethoxylated glycerol, sorbitan esters, etc.

In the patent application EP-A-684302 are described aqueous nacreous compositions having non-ethoxylated esters of polyglycerol as crystallisation adjuvants of the nacreous agent.

It is clear that the problem of obtaining concentrate nacreous compositions still requires new solutions to obtain easier and cheaper compositions with a higher effectiveness.

SUMMARY OF THE INVENTION

The present invention provides new aqueous nacreous concentrated compositions, containing ethoxylated glycerides derived from carboxylic acids having 6 to 22 carbon atoms as emulsifying and/or dispersing agent, and showing a good storage stability, appropriate viscosity for handling and pumping, excellent nacreous appearance and resistance to bacterial contamination, besides the possibility of acting as thickening agent and increasing the foaming power of personal hygiene cosmetic products.

The present invention also provides the use of the mentioned aqueous nacreous concentrated compositions as nacreous additives in personal hygiene cosmetic products.

The aqueous nacreous concentrate compositions of the present invention comprise, expressed as weight percentage, the following essential components
i) 3–15% of an ester type nacreous agent with the following formula

$$R^1-(OCH_2CH_2)_n-OR^2 \tag{I}$$

in which $R^1$ is a linear or branched fatty R—CO group where R has 16 to 22 carbon [to make sure that 16 and 22 are included] atoms, $R^2$ being hydrogen or an $R^1$ group, n being a number from 1 to 5
ii) 10–20% of an anionic surfactant selected from the alkyl ether sulfates type having an alkyl chain from 10 to 18 carbon atoms
iii) 20–40% of ethoxylated glycerides derived from carboxylic acids having 6 to 22 carbon atoms
wherein the total organic content is higher than 40% weight.

DESCRIPTION OF THE INVENTION

The ester type nacreous agents with the following formula (I) $R^1-(OCH_2CH_2)_n-OR^2$ that can be used are, for example, monoesters and diesters of ethylene glycol with higher fatty acids having a linear or branced RCO group having 16 to 22 carbon atoms, like palmitic acid, stearic acid, arachidic acid, behenic acid, or unsaturated higher fatty acids, like oleic acid, linoleic acid or erucic acid. Also suitable are mixtures of monoester and diesters of diethylene glycol with those fatty acids.

Preferred nacreous agents are those containing glycol monoesters and/or diesters having an alkyl chain $C_{16}$–$C_{18}$. Even more preferred are those glycol esters having a weight ratio of di-ester to mono-ester ranging from 85:15 to 98:2, more preferably from 93:7 to 97:3.

Particularly preferred as nacreous agent is a mixture of ethylene glycol distearate (INCI name, International Nomenclature Cosmetic Ingredient, Glycol Distearate), and ethylene glycol monostearate (INCI name, Glycol Stearate), having a weight ratio of di-ester to mono-ester higher than 94%.

Among the suitable nacreous agents according to the invention are commercially available agents such as EMANON® 3201 (INCI name, Glycol Distearate), supplied by the company KAO Corporation, S.A.

Suitable anionic surfactants selected from the alkyl ether sulfates type having an alkyl chain from 10 to 18 carbon atoms are the metallic salts of said alkyl ether sulfates as well as the ammonium salts or salts of organic amines having one or more alkyl or hydroxyalkyl groups.

Preferred anionic surfactants, selected from the alkyl ether sulfates type, are sodium alkyl ether sulfates having an average degree of ethoxylation in the range of 0.5 to 7, more preferred in the range of 1 to 5, and having an alkyl chain from 10 to 18 carbon atoms, more preferred 12 to 16 carbon atoms.

Particularly preferred as anionic surfactant is sodium lauryl ether sulfate (INCI name, Sodium Laureth Sulfate), preferably with an average degree of ethoxylation in the range of 1 to 3, more preferably from 1 to 2.5, and even more preferably from 2 to 2.5.

The total content of anionic surfactant in the compositions according to the invention can be in the range of 10% to 20% by weight, preferably from 12% to 18%.

Among the suitable anionic surfactants according to the invention two could be mentioned. They are commercially available under the trademarks EMAL® 270D and EMAL® 270E (INCI name, Sodium Laureth Sulfate), having a 70% active matter and an average degree of ethoxylation of 2, supplied by KAO Chemicals GmbH and KAO Corporation, S.A.

Preferred ethoxylated glycerides derived from carboxylic acids, having 6 to 22 carbon atoms, include the compounds described in the European patent application EP-A-1045021, represented by formula (II).

(Formula II):

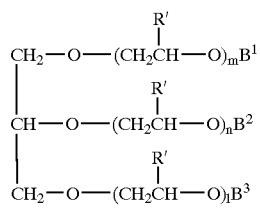

R′ represents H or $CH_3$, and each m, n, and l, independently, represents a number from 0 to 4. The sum of m, n and l being in the range from 1 to 4, each B1, B2, and B3 independently representing H or an acyl group having 6 to 22 carbon atoms, with the provision that at least one B1, B2 or B3 is an acyl group having 6 to 22 carbon atoms.

The ethoxylated glycerides are preferably used as a mixture of the compounds represented by formula (II), comprising (i) compounds represented by the before formula (II), where each B1, B2 and B3, independently, represent an acyl group having 6 to 22 carbon atoms;
(ii) compounds represented by the before formula (II), where two of B1, B2 and B3, independently, represent an acyl group having 6 to 22 carbon atoms, the remainder representing H;
iii) compounds represented by the before formula (II), where one of B1, B2 and B3, independently, represent an acyl group having 6 to 22 carbon atoms, the remainder representing H;
iv) compounds represented by the before formula (II), where each of B1, B2 y B3 represent H; the weight ratio of the compounds (iii)/(ii)/(i) being 46-90/9-35/1-15.

These compounds are prepared as it is described in the European patent application EP-A-1045021, preferably by reaction of triglycerides, glycerine and ethylene oxide.

The acyl group, having 6 to 22 carbon atoms, preferably from 12 to 18 carbon atoms, is preferably derived from natural fat and oil as well as synthetic triglycerides. Preferred fats and oils include palm oil, coconut oil, sunflower oil, rapeseed oil, castor oil, olive oil, soybean oil; and animal fat such as tallow, bone oil; fish oil, hardened oils and semihardened oils thereof; and mixtures thereof. Particularly preferred are acyl groups derived from coconut oil, palm oil and tallow such as beef tallow.

Among the suitable ethoxylated glycerides according to the invention it could be mentioned one, commercially available under the trademark LEVENOL® H&B (INCI name, Glycereth-2 cocoate), supplied by the company KAO Corporation, S.A. It is a mixture of compounds represented by the formula (II), where the sum of m, n and l is 2 and either B1 or B1 and B2 are acyl groups derived from coconut oil.

The total content of ethoxylated glycerides in compositions according to the invention can be in the range of 20% to 40% weight, preferably 22% to 35%.

The preferred aqueous nacreous concentrate compositions comprise
i) 7% to 12% weight of a nacreous agent as described before
ii) 12% to 18% weight of an anionic surfactant as described before
iii) 22% to 35% weight of ethoxylated triglycerides as described before wherein the total organic content is higher than 45% weight.

The pH value of the aqueous nacreous compositions is preferably in the range of 4 to 8.

The concentrate compositions of the present invention are preferably free from alkanolamides. Moreover, the concentrate compositions of the present invention are preferably free from preservatives.

The aqueous nacreous concentrate compositions subject of the present invention can be obtained following well known methods to the skilled in the art. For example, the most common process for obtaining these types of compositions is based on heating the components to 70–80° C. and then gradually cooling them, following a defined cooling rate, to produce the crystallisation of the nacreous agent.

The obtained compositions can be used as nacreous additives in personal hygiene formulations. When incorporated into typical surfactant bases used in the personal hygiene products, higher viscosities are obtained with lower electrolyte concentration, therefore it can be concluded that the nacreous concentrates subject of the present invention show a viscosizing effect. On the other hand, adding less electrolyte means that the obtained cosmetic products are less irritant to the skin and to the eyes.

Furthermore, after adding nacreous concentrates, subject of the present invention, to typical surfactant bases of personal hygiene cosmetic products, an increase of the foaming power of the cosmetic product is observed.

The use of the before-mentioned aqueous nacreous concentrate compositions as nacreous additives in personal hygiene cosmetic products is also included in the subject of the present invention. The use of the compositions of the present invention in personal hygiene cosmetic products is particularly preferable in view of their moisturizing and emollient effect on human hair and human skin.

The amount of aqueous nacreous concentrate to add to personal hygiene cosmetic products depends on several factors, however, it can be concluded that a suitable nacreous appearance can be obtained when the amount of nacreous concentrate is between 1% and 10% with regards to the weight of the cosmetic product.

The composition of the present invention may optionally contain further ingredients such as colorants.

The following examples are given in order to provide a person skilled in the art with a sufficiently clear and complete explanation of the present invention, but should not be considered as limiting of the essential aspects of its subject, as set out in the preceding portions of this description.

EXAMPLES

Example 1

Preparation of the Nacreous Concentrates of the Invention 1.1.—General Method

The compositions described in the invention have been obtained in accordance with the following method: deionized water, an anionic surfactant and the ethoxylated glycerides are introduced in a closed reactor with agitation. It is stirred until a homogeneous mixture is obtained and it is heated up to 80° C. Afterwards the nacreous agent is added to this mixture and it is stirred until a homogeneous mixture is obtained. Subsequently, a controlled cooling starts, decreasing the temperature from 80° C. to 30° C. over 2 hours approximately.

1.2.—Prepared Compositions

Following the general method the compositions A, B, C, D, E, F, N and O described in table 1 are prepared, where the quantities of the components are indicated in weight percentage, balancing to 100 with deionized water.

The components used in the table are the market products described in the description of the invention and their names are:

Emal® 270E, sodium lauryl ether sulfate, having 70% of active matter and an average ethoxylation degree of 2

Emanon® 3201, ethylene glycol distearate with an ethylene glycol monostearate content not higher than 6% in weight Levenol® H&B, ethoxylated glycerides with an average ethoxylation degree of 2 ethylene oxide mol per glycerine mol, and having acyl groups deriving from coconut oil.

Example 2

Evaluation Methods 2.1.—Appearance: Nacreous Effectiveness

The evaluation of the nacreous effectiveness of the concentrated, described in the above mentioned example, has been done according to the following methods:

(a) Naked Eye Observation

The nacreous concentrate was observed by the naked eye in its original state and diluted, always in comparison with a standard.

To prepare the dilution, the nacreous concentrate was dispersed in a concentration of 3% by weight in deionized water and it was added 1 mL of an 1% aqueous solution of a red colorant to facilitate the observation.

The evaluated parameters were:

Nacreous appearance: Iridescent or nacreous appearance and brightness

Opacifying effect: opacity degree

Sedimentation speed: how iridescent appearance disappears or slows down after agitating the nacreous solution (b) Measurement of Particle Size The particle size of the nacreous concentrate was measured in a dispersion thereof in deionized water using a laser light scattering based particle sizer (MasterSizer MS1002). The type of dispersion to use will be defined by the methodology given by the supplier, e.g. the cell system, the quantities of the sample required, the preparation of the dispersion etc. In general, the nacreous concentrated is added to a small cask containing water.

The distribution size (particle size distribution or PSD) is indicated as the average diameter of the whole distribution expressed in volume (D[4, 3]).

TABLE 1

Aqueous nacreous concentrated compositions

| Components | A | B | C | D | E | F | N | O |
|---|---|---|---|---|---|---|---|---|
| Emal ® 270E | 24.6 | 22.7 | 22.7 | 20.8 | 20.8 | 19 | 14.5 | 14.5 |
| Emanon ® 3201 | 15 | 10 | 15 | 10 | 15 | 10 | — | 3 |
| Levenol ® H&B | 20 | 25 | 25 | 30 | 30 | 35 | 23 | 23 |
| Ethylene glycol (di/mono) stearate(ratio 2:1) | — | — | — | — | — | — | 3 | — |
| Palmitic acid | | | | | | | 6 | 6 |
| Stearic acid | | | | | | | 6 | 6 |
| KOH (25 wt. % in water) | | | | | | | 0.025 | 0.025 |
| p-hydroxy benzoic acid ester (Phenonip ®) | | | | | | | 0.2 | 0.2 |
| Deionized Water | to 100 | to 100 | to 100 | to 100 | to 100 | to 100 | to 100 | to 100 |

(c) Observation with an Optical Microscope

The appearance of the concentrated product and the aqueous dispersion was observed with an optical microscope using a polarised light filter.

2.2.—Viscosity Determination

The viscosity measurements were done using an "infinite sea" rotary viscometer (Brookfield LVT) (see X. Domingo "A guide to the surfactants world", Ed. Proa, SA, 1995).

2.3.—Stability

The stability has been evaluated at different temperatures for the concentrates B, C and D of example 1 (40° C., room temperature and 5° C.) for a long period of time (1 month), observing the changes in appearance and in physico-chemical properties (pH, viscosity, . . . ).

The results are shown in tables 2 and 3.

TABLE 2

Results of the nacreous appearance test and viscosity test

| | Concentrates | | | | | |
|---|---|---|---|---|---|---|
| | A | B | C | D | E | F |
| Form | FP | VL | FP | VL | FP | FP |
| Appearance | ++++ | +++++ | +++++ | +++++ | +++++ | +++++ |
| Appearance at 3% aq. sol. | +++++ | +++++ | +++++ | +++++ | +++++ | +++++ |
| Opacity | ++++ | +++++ | +++++ | +++++ | ++++ | ++++ |

TABLE 2-continued

Results of the nacreous appearance test and viscosity test

| | Concentrates | | | | | |
|---|---|---|---|---|---|---|
| | A | B | C | D | E | F |
| Viscosity (cP) 20° C. Spd 4, 12 rpm | 25400 | 11700 | 13200 | 10400 | 23400 | 28500 |
| PSD D (4,3) μm | 10.2 | 13.00 | 13.78 | 19.3 | 10.21 | 15.8 |

P: Paste;
FP: Fluid Paste;
VL: Viscous Liquid
+++++: Excellent,
++++: Good,
+++: Fair,
++: Bad,
+: Very Bad The following evaluations use, as a sample, the nacreous concentrates B, C and D from example 1.

TABLE 3

Results of nacreous appearance test, stability test and viscosity test of the concentrates B, C and D

| | Concentrates | | | | | | | | |
|---|---|---|---|---|---|---|---|---|---|
| | B | | | C | | | D | | |
| Appearance | +++++ | | | +++++ | | | +++++ | | |
| Appearance at 3% aq. sol. | +++++ | | | +++++ | | | +++++ | | |
| pH (5%) | 7.32 | | | 7.15 | | | 7.42 | | |
| Viscosity (cP) 20° C. Spd 4, 12 rpm | 11700 | | | 13200 | | | 10400 | | |
| Apparent density g/cm³ | 1.03–1.04 | | | 1.03 | | | 1.03–1.05 | | |
| PSD D [4,3] μm | 13.00 | | | 13.78 | | | 19.27 | | |
| Stability | 40° C. | Room temp | 5° C. | 40° C. | Room temp | 5° C. | 40° C. | Room temp | 5° C. |
| Appearance | +++++ | +++++ | +++++ | +++++ | +++++ | +++++ | +++++ | +++++ | +++++ |
| pH | 7.13 | 7.29 | 7.30 | 7.02 | 7.27 | 7.18 | 7.20 | 7.33 | 7.32 |
| Viscosity | 10800 | 11500 | 11400 | 12700 | 15300 | 12300 | 9100 | 9520 | 10500 |

+++++: Excellent,
++++: Good,
+++: Fair,
++: Bad,
+: Very Bad

As was evidenced from the results, the nacreous appearance of the developed nacreous concentrates is characterised by a bimodal type particle size distribution centred on 10–20 μm, with a small remainder or bottom centred on 1 μm approximately, that can be associated to its good opacifying effectiveness as well as good nacreous effectiveness.

The homogeneity of the crystal structure can be easily confirmed by using an optical microscope with a light polarised filter.

On the other hand, the stability after 1 month at 40° C., room temperature (Room temp) and 5° C. remains correct in all the compositions and neither separations nor pH or significant viscosity variations were observed.

Example 3

Evaluation Methods (2)

3.1.—Self-Preserving Capacity

Self-preserving evaluation of nacreous concentrates B,C, and D of example 1.

25 g. samples of different nacreous concentrates (B,C and D) were prepared. Samples were incubated at 20° C. during 5 days before use. EMAL® 227E (supplied by KAO Corporation, S.A., INCI name: Sodium Laureth Sulfate, 27% active matter) with addition of a well-known preservative was used as control sample.

A mixture suspension of micro-organisms was prepared in sterile saline solution to give a microbial count of approximately $10^9$ cfu/mL. The following micro-organisms were employed: *Pseudomonas aeruginosa* ATCC 15442, *Pseudomonas putida* (Kao Corporation S.A. strain no. 12; in-house micro-organism), *Serratia liquefaciens* (Kao Corporation S.A. strain no. 18; in-house micro-organism), *Enterobacter gergorviae* (Kao Corporation S.A. strain no. 20; in-house micro-organism), organism), and *Aspergillus niger* ATCC 16404. All of these strains (except *A. niger*) showed growth in surfactant products. 0.1 mL of microbial suspension was inoculated in the nacreous concentrate samples (25 g.). Challenge formulations were sampled for viable count of micro-organismsat selected time intervals to know microbial load of each sample, following the method "Determination of the microbiological content of cosmetic products" described in the CTFA Microbioloby Guidelines, published in 1993 by the Cosmetic, Toiletry, and Fragrance Association, Inc.

TABLE 4

| Concentrate | Plate viable counts (cfu/mL.) | | | |
|---|---|---|---|---|
| | 4 hours | 8 hours | 24 hours | 7 days |
| B | >250 | >250 | <10 | <10 |
| C | >1000 | >250 | <10 | <10 |
| D | >250 | >250 | <10 | <10 |
| Control | >1000 | >250 | <10 | <10 |

This study was repeated later with the following micro-organisms: *Pseudomonas aeruginosa* ATCC 15442, *Enterobacter sakazakii* (Kao Corporation S.A. strain no. 16; in-house micro-organism), *Serratia liquefaciens* (Kao Corporation S.A. strain no. 18; in-house micro-organism), *Escherichia coli* ATCC 10536 and *Aspergillus niger* ATCC 16404.

TABLE 5

| Concentrate | Plate viable counts (cfu/mL.) | | |
|---|---|---|---|
| | 6 hours | 24 hours | 7 days |
| B | >1000 | <10 | <10 |
| C | >1000 | >1000 | <10 |
| D | >1000 | <10 | <10 |
| Control | >1000 | >1000 | <10 |

As a conclusion all samples are able to eliminate micro-organisms (Gram negative and fungi) in a short period of time. Some micro-organisms are eliminated faster in samples C and D. According to this study, nacreous concentrates subject of the present invention do not need any preservative to assure protection against micro-organisms.

3.2.—Evaluation of the Viscosity-Rheology

The evaluation of the rheological behaviour is an indirect measurement of the consistency and quality of the product, besides being a direct method to assess handiness of nacreous concentrates at different temperatures.

The viscosity measurements were done using an "infinite sea" rotary viscometer (Brookfield LVT, spindle 4).

The used nacreous concentrate was B from example 1.

From the experimental results it can be deduced that the apparent viscosity of the nacreous concentrates subject of the present invention, presents a slight variation in a wide range of temperatures (0° C. to 45° C.).

For the evaluation of the rheological behaviour of the nacreous concentrate B from example 1, a Brookfield LVT viscometer was also used, at 20° C. and spindle 4, for one minute. In this case the shear rate was increased and afterwards decreased.

From the experimental results it can be concluded that the rheological behaviour of the nacreous concentrate B is typically pseudoplastic (typical behaviour of the colloidal systems), it is constant at different temperatures and does not show thixotropy (decreasing of the viscosity with time). It shows a fluency threshold (initial force that has to be applied to a plastic fluid to start flowing) of 150–300 mPa.

For all of this, it can be said that the nacreous concentrates subject of the present invention are products easy to handle.

Example 4

Application in Personal Hygiene Products

The incorporation of the nacreous concentrates subject of the present invention in a typical surfactant base used in the personal hygiene products was studied.

The base was the following:
Sodium lauryl ether sulfate (INCI name, Sodium Laureth Sulfate): 12% active matter
Coco amido propyl betaine (INCI name, Cocamidopropyl Betaine) 1.8% active matter
Etoxylated monoethanolamide fatty acid (INCI name, PEG-4 Rapeseed amide) 1.5% active matter
Nacreous concentrate B 2% and 4% by weight 4.1—Thickening-Effect The effect of incorporating these nacreous concentrates to the viscosity of the personal hygiene product described above has been studied. A Brookfield LVT viscometer was used, at 20° C. of temperature.

After adding a nacreous concentrate (concentrate B from example 1) to a typical surfactant base used in personal hygiene cosmetic products as the one described above, higher viscosity values were obtained for lower electrolyte concentrations (sodium chloride was used, due to the fact that it is the most commonly used in personal hygiene formulations). As a result it can be concluded that the nacreous concentrates subject of the present invention show certain viscosizing effect.

On the other hand, adding this type of nacreous concentrates allows to decrease the amount of electrolyte used to adjust the viscosity of the personal hygiene formulations. As a result, it is predictable that these kind of cosmetic products will be less irritating than the ones using a normal amount of electrolyte.

4.2.—Foaming Power

The effect of incorporating a nacreous concentrate (concentrate B from example 1) to the foaming power of personal hygiene products, as described above, has been studied.

To determine the foam volume, the method "Reverse Stirring Agitation" has been used, method which consists in measuring foam volume after agitation of 100 g of a solution of the product to assay, located in a graduated cylinder of 400 mL of capacity, with a metallic stirrer at 1100 r.p.m., changing the direction every 6 seconds during 5 minutes. The determination of the foam volume was performed at 40° C., using water of 20° f (French degrees) of water hardness, with a $Ca^{2+}:Mg^{2+}$ ratio of 2:1. The aim of this method is to evaluate the foam behaviour of compositions destined to personal hygiene in the presence of dirtiness.

TABLE 6

Foaming power of a typical surfactant base after incorporating a nacreous concentrate (Method "Reverse Stirring Agitation")

| | 0 g sebum Concentrate | | | 0.5 g sebum | | |
|---|---|---|---|---|---|---|
| | 0% conc. B | 2% conc. B | 4% conc. B | 0% conc. B | 2% conc. B | 4% conc. B |
| Foam Volume (mL) | 198 | 209 | 211 | 95 | 112 | 130 |

The measures were taken after 30 seconds in duplicate. The values shown in table 6 are the average of the obtained results.

As was clearly evidenced from the results, the foam behaviour of the cosmetic product is higher after incorporating a nacreous concentrate of the present invention even after the addition of a certain amount of "sebum" (artificial mixture of lipids similar to the sebaceous human layer), as it can be seen in table 6.

Example 5

Comparative Tests (1)

As mentioned before, the European patent application EP-A-300379 describes nacreous concentrate compositions free from fatty alkanolamides.

To evaluate the nacreous appearance and the handling of the concentrates of the present invention, comparative assays were performed between composition B from example 1 and the compositions described in examples 2, 6, 7, 8, 9, 10, 18, 20, 21, 22 and 23 of the above mentioned patent application. The compositions to be evaluated were obtained following the description of such patent application.

The results are shown in table 7 and 8.

TABLE 7

Results of the evaluation tests concerning nacreous appearance, viscosity and particle size (1)

| | B | Ex. 2 | Ex. 6 | Ex. 7 | Ex. 8 | Ex. 9 | Ex. 10 |
|---|---|---|---|---|---|---|---|
| Form | Viscous Liquid | White emulsion that easily separates | White emulsion having big particles in suspension | White non-fluid paste | White emulsion having big particles in suspension | White fluid paste | White fluid paste |
| Nacreous appearance | +++++ | + | + | + | + | + | + |
| Nacreous appearance at 3% | +++++ | + | + | + | + | + | + |
| Opacity (3%) | +++++ | + | + | ++ | ++ | + | + |
| Viscosity 20° C., 12 rpm | spd4 11700 | spd4 15000 | spd3 7210 | spd4 — | spd3 8930 | spd4 18496 | spd4 17496 |
| PSD D [4,3] $\mu$m | 13.00 | 12.50 | 25.35 | 13.77 | 28.09 | 31.59 | 35.8 |

+++++: Excellent,
++++: Good,
+++: Fair,
++: Bad,
+: Very Bad

TABLE 8

Results of the evaluation tests concerning nacreous appearance, viscosity and particle size (2)

| | Ex. 18 | Ex. 20 | Ex. 21 | Ex. 22 | Ex. 23 | N | O |
|---|---|---|---|---|---|---|---|
| Form | Very liquid white emulsion | White fluid paste | White fluid emulsion | White fluid emulsion | Very liquid white emulsion | Paste | Paste |
| Nacreous appearance | +++ | +++ | ++ | + | + | + | ++ |

TABLE 8-continued

Results of the evaluation tests concerning
nacreous appearance, viscosity and particle size (2)

|  | Ex. 18 | Ex. 20 | Ex. 21 | Ex. 22 | Ex. 23 | N | O |
|---|---|---|---|---|---|---|---|
| Nacreous appearance at 3% | +++ | +++ | ++ | + | + | +++ | +++ |
| Opacity (3%) | ++ | +++ | ++ | + | + | + | + |
| Viscosity 20° C., 12 rpm | spd4 4949 | spd4 18996 | spd4 7010 | spd3 6629 | spd3 2879 | — | — |
| PSD D [4,3] µm | 28.54 | 35.49 | 11.68 | 14.49 | 30.61 | 27.69 | 28.03 |

+++++: Excellent,
++++: Good,
+++: Fair,
++: Bad,
+: Very Bad

To evaluate the nacreous appearance and the opacity of the compositions, 3% in weight of the nacreous concentrates were dispersed in deionized water and it was added 1% in weight of a red colorant to facilitate the observation.

From the experimental results it can be concluded that the nacreous concentrates, subject of the present invention, exhibit an improved nacreous appearance compared to the ones described in the prior art. Besides, they have generally a better fluidity, and, therefore, can be pumped easily. The comparison of Example N with Examples 22 and 23 of EP-A-300379 reveals the advantages of the compositions of the present invention over these prior art compositions with respect to the appearance after dilution (3% aqueous solution) When using ethylene (di/mono) stearate having a di/mono ratio of larger than 94/6 (Example O) instead of one with a ratio of 2:1 (Example N), the appearance is improved further.

Example 6

Comparative Tests (2)

Other ethoxylated glycerides were evaluated. Composition C from example 1 was used as a standard, and following the method described in example 1, several nacreous concentrates were obtained as it is shown in table 9.

| Emal ® 270E | 22.7 |
|---|---|
| Emanon ® 3201 | 15 |
| Ethoxylated glyceride | 25 |
| Deionized water | to 100 |

All the products mentioned before are mixtures of compounds represented by the formula (II), where the sum of m, n and l is variable and the acyl groups are derived from the coconut oil.

All the compounds were supplied by KAO Corporation, S.A.

The results are shown in table 10.

TABLE 10

Nacreous appearance and viscosity results

|  | C | G | H | I | J |
|---|---|---|---|---|---|
| Form | Fluid Paste | Fluid Paste | Paste | Paste | Fluid Paste |
| Nacreous appearance | +++++ | +++ | + | ++++ | + |
| Nacreous appearance at 3% | +++++ | ++++ | + | ++++ | ++ |
| Opacity (3%) | +++++ | +++ | + | +++ | +++ |
| Viscosity 20° C., spd4, 12 | 13200 | 25200 | — | — | 44800 |
| PSD D [4, 3] µm | 13.78 | 5.39 | — | 10.78 | 12.37 |

+++++: Excellent,
++++: Good,
+++: Fair,
++: Bad,
+: Very Bad

The viscosity of the concentrates H and I was not determined because they were in a paste form.

As it was evidenced from the results, it can be concluded that the mixtures have, in some cases, an optimal nacreous

TABLE 9

Ethoxylated glycerides used for the tests

| | Concentrates | | | | |
|---|---|---|---|---|---|
|  | C | G | H | I | J |
| Ethoxylated glycerides | Levenol ® H&B | Levenol ® C-642 | Levenol ® C-201 | Levenol ® C-301 | Emanon ® HE |
| INCI Name | Glycereth-2 Cocoate | Glycereth-5 Cocoate | Glycereth-17 Cocoate | Glycereth-7 Cocoate | PEG-7 Glyceryl Cocoate |
| m + n + l | 2 | 5 | 17 | 7 | 7 | appearance, but lower than the one obtained for concentrate C. On the other hand, the viscosity would be in the upper limit advisable for this type of products, something that would impede fluidity and, therefore, make pumping difficult.

Example 7

Comparative Tests (3)

Other formulations were evaluated using the same components as described in example 1, but in different ratios, and taking as a reference the nacreous concentrate A of example 1.

Following the general method compositions K, L and M were prepared as described in table 11, where the quantities of the components are indicated in weight percentage, balancing to 100 with deionized water.

TABLE 11

Aqueous nacreous concentrate compositions

| | Components | | | |
|---|---|---|---|---|
| | K | L | M | A |
| Emal ® 270E | 30.3 | 21.4 | 26.6 | 24.6 |
| Emanon ® 3201 | 15 | 15 | 15 | 15 |
| Levenol ® H&B | 5 | 10 | 15 | 20 |
| Deionized water | to 100 | to 100 | to 100 | to 100 |

The components used in the table are the market products described in the description of the invention and, as mentioned before, were supplied by KAO Corporation, S.A.

To perform the evaluation the methods described in example 2, referred to the nacreous effectiveness (heading 2.1), were followed.

TABLE 12

Results of nacreous appearance test and viscosity test

| | Concentrates | | | |
|---|---|---|---|---|
| | K | L | M | A |
| Form | P | P | P | FP |
| Nacreous appearance | + | + | +++ | ++++ |
| Nacreous appearance at 3% | + | + | ++++ | +++++ |
| Opacity | + | + | ++++ | ++++ |
| Viscosity (cP) 20° C. Spd 4, 12 rpm | — | — | — | 25400 |
| PSD D (4,3) μm | 4.42 | 11.17 | 7.67 | 10.2 |

P: Paste;
FP: Fluid Paste;
VL: Viscous Liquid
+++++: Excellent,
++++: Good,
+++: Fair,
++: Bad,
+: Very Bad The viscosity of the concentrates K, L and M were not determined because they were in a paste form.

As it was evidenced from the results, it can be concluded that concentrates K and L show a nacreous appearance much lower than the one shown by concentrate A. Although the nacreous appearance shown by concentrate M, is optimum, concentrates K and L show such a high viscosity that

What is claim is:

1. Aqueous nacreous concentrate compositions comprising, expressed as weight percentage, the following essential components (i) 3–15% of an ester nacreous agent with the following formula $$R^1-(OCH_2CH_2)_n-OR^2 \quad (I)$$

in which $R^1$ is a linear or branched fatty R—CO group where R has 16 to 22 carbon atoms, $R^2$ being hydrogen or an $R^1$ group, n being a number from 1 and 5

(ii) 10–20% of an alkyl ether sulfate anionic surfactant having an alkyl chain from 10 to 18 carbon atoms (iii) 20–40% of ethoxylated glycerides derived from carboxylic acids having 6 to 22 carbon atoms wherein the total organic content is higher than 40% weight.

2. Aqueous compositions according to claim 1, wherein the nacreous agent is glycol mono- and/or di-esters having an $C_{16}$–$C_{18}$ alkyl chain.

3. Aqueous compositions according to claim 2, wherein the nacreous agent is selected from a mixture of ethylene glycol monostearate and ethylene glycol distearate.

4. Aqueous compositions according to claim 2, wherein the glycol esters have a ratio in weight of di-ester to mono-ester from 85:15 to 98:2.

5. Aqueous compositions according to claim 4, wherein glycol esters have a ratio in weight of di-ester to mono-ester from 93:7 to 97:3.

6. Aqueous compositions according to claim 1, wherein the anionic surfactant is sodium lauryl ether sulfate having an alkyl chain having 10 to 18 carbon atoms and having an average degree of ethoxylation in the range of 0.5 to 7.

7. Aqueous compositions according to claim 6, wherein the sodium lauryl ether sulfate has an alkyl chain having 12 to 16 carbon atoms and an average degree of ethoxylation in the range of 1 to 5.

8. Aqueous compositions according to claim 7 wherein the anionic surfactant is sodium lauryl ether sulfate having an average degree of ethoxylation in the range of 1 to 3.

9. Aqueous compositions according to claim 1, wherein the ethoxylated glycerides derived from carboxylic acids having 6 to 22 carbon atoms comprise the compounds represented by the formula (Formula II):

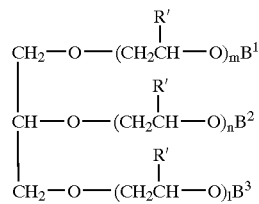

R' representing H or $CH_3$, and each m, n, and l independently representing a number from 0 to 4, the sum of m, n and l being in the range of 1 to 4, and where B1, B2, and B3 independently represent H or an acyl group having 6 to 22 carbon atoms, with the proviso that, at least, one B1, B2 and B3 group is an acyl group having 6 to 22 carbon atoms.

10. Aqueous compositions according to claim 9, wherein the sum of m, n and l is in the range of 1.5 to 3.0.

11. Aqueous compositions according to claim 1, comprising
- (i) 7–12% of nacreous agent
- (ii) 12–18% of anionic surfactant
- (iii) 22–35% of ethoxylated glycerides wherein the total organic content is higher than 45% in weight.

12. Aqueous compositions according to claim 1, wherein the composition has a pH value in the range of 4 to 8.

13. A personal health care product comprising the aqueous composition according to claim 1 as a nacreous additive.

* * * * *